US007408075B1

(12) United States Patent
Rezanka

(10) Patent No.: US 7,408,075 B1
(45) Date of Patent: Aug. 5, 2008

(54) SYNTHESIS OF PHOSPHOCHOLINE ESTER DERIVATIVES AND CONJUGATES THEREOF

(75) Inventor: Louis J Rezanka, Baltimore, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 72 days.

(21) Appl. No.: 11/385,514

(22) Filed: Mar. 21, 2006

Related U.S. Application Data

(60) Provisional application No. 60/664,716, filed on Mar. 23, 2005.

(51) Int. Cl.
*G07F 9/09* (2006.01)
(52) U.S. Cl. ............................ 558/172; 558/70; 558/87; 558/111; 558/170
(58) Field of Classification Search .................. 514/78; 558/111, 70, 87, 170, 172
See application file for complete search history.

(56) References Cited

U.S. PATENT DOCUMENTS

| 5,455,032 | A  | 10/1995 | Kenny et al. ............. 424/194.1 |
| 6,376,203 | B1 | 4/2002  | Matsuda et al. ............ 435/7.32 |
| 2004/0156864 | A1 | 8/2004 | Birkett .................... 424/189.1 |

OTHER PUBLICATIONS

Thomas F Spande Synthesis of Two Novel Phosphorylcholine Esters for Probes in Immunological Studies J. Org. Chem. 1980, 45, 3081-3084.*
Pawel Knopik, Karol S Bruzik, and Wojciech J. Stec An improved synthesis of 6-(O-Phosphorylcholine)hydroxyhexanoic acid Organic preparations and procedures international (OPPI Briefs) vol. 23, No. 2, 1991 pp. 214-216.*
Ames, B. N. et al., "The Role of Polyamines in the Neutralization of Bacteriophage Deoxyribonucleic Acid", *Journal of Biological Chemistry*, 1960, 235(3), 769-775.
Chesebro, B. et al., "Affinity Labeling of a Phosphorylcholine Binding Mouse Myeloma Protein", *Biochemistry*, 1972, 11(5), 766-771.
Fischer,. T. et al., "A Novel Phosphocholine Antigen Protects both Normal and X-Linked Immune Deficient Mice against *Streptococcus pneumoniae*", *The American Association of Immunologists*, 1995, 3371-3382.
Guo, W-X. et al., "Sequence Changes at the V-D Junction of the Vh1 Heavy Chain of Anti-Phosphocholine Antibodies Alter Binding to and Protection against *Streptococcus pneumoniae*", *International Immunology*, 1996, 9(5), 665-677.
Kenny, J.J. et al., "Induction of Phosphocholine-Specific Antibodies in X-Linked Immune deficient Mice: *in Vivo Protection* against a *Streptococcus pneumoniae* Challenge", 1993, 6(4), 561-568, International Immunology.
Langer, R., "New Methods of Drug Delivery", *Science*, 1990, 249, 1527-1533.
Matsuda, K. et al., "Structure of a Novel Phosphocholine-Containing Glycoglycerolipid from *Mycoplasma fermentans*", *The Journal of Biological Chemistry*, 1994, 269(52), 33123-33128.
Mi, Q-S. et al., "Highly Reduced Protection against *Streptococcus pneumoniae*after Deletion of a Single Heaby Chain Gene in Mouse", *PNAS*, 2000, 97(11), 6031-6036.
Spande, T.F., "Synthesis of Two Novel Phosphorylcholine Esters for Probes in Immunogenic Studies", *J. Org. Chem.*, 1980, 45, 3081-3084.
Spande, T.F., "Synthesis of Two Novel Phosphorylcholine Esters for Probes in Immunological Studies", *J. Org. Chem.*, 1980, 45, 3081-3084.
Wicker. L.S. et al., "Antibodies from the Lyb-5-B Cell Subset Predominate in the Secondary 1gG Response to Phosphocholine", *Journal of Immunology*, 1982, 129(3), 950-953.
Wicker, L.S. et al., "The Asymmetry in Idiotype-Isotype Expression in the Reposne to Phosphocholine is Due to Divergence in the Expressed Repertoires of Lyb-5+ and Lyb-5-B Cells", *Journal of Immunology.*, 1982, 131(5), 2468-2476.

\* cited by examiner

*Primary Examiner*—Shailendra Kumar
(74) *Attorney, Agent, or Firm*—Woodcock Washburn LLP

(57) ABSTRACT

Aspects of the present invention include methods of synthesizing phosphocholine analogues and the phosphocholine conjugates formed therefrom and their use in preventing infections caused by microorganisms.

19 Claims, No Drawings

SYNTHESIS OF PHOSPHOCHOLINE ESTER DERIVATIVES AND CONJUGATES THEREOF

CROSS REFERENCE TO RELATED APPLICATIONS

The application claims the benefit of U.S. Provisional Application No. 60/664,716 filed Mar. 23, 2005, which is hereby incorporated by reference in its entirety.

STATEMENT OF FEDERALLY SPONSORED RESEARCH

The U.S. Government may have certain rights in the invention described herein, which was made in part with funds from NIH Contract No. 263-02-D-0053.

FIELD OF THE INVENTION

The present invention relates to methods of synthesizing phosphocholine ester derivatives useful for, inter alia, protection against pathogenic microorganisms.

BACKGROUND OF THE INVENTION

Phosphocholine conjugates have been studied extensively because phosphocholine (PC) is thought to play a vital role in the pathogenesis of pathogenic microorganisms, such as *Streptococcus pneumoniae*. Some reports suggest that by binding to the platelet activating factor receptor on epithelial and endothelial cells, PC facilitates transport of *S. pneumoniae* into the blood and brain. Furthermore, PC has been found to be an immunodominant epitope on the surface of many pathogenic microorganisms, including but not limited to *S. pneumoniae, Streptococcus oralis, Streptococcus sanguis, Streptococcus* spp., *Clostridium* spp., *Lactococcus* spp., *Bacillus* spp., *Haemophilus influenzae, Haemophilus aphrophilus, Proteus morganii, Actinomyces naeslundii, Actinobacillus actinomycetemcomitans, Fusobacterium nucleatum, Neisseria meningitidis, Trichinelia spiralis, Acanthocheilonema viteae, Leishmania major, Trypanosoma cruzi, Schistosoma mansoni, Diphyllobothrium latum, Toxicara canis* (second stage larvae), *Acanthocheilonema viteae*, and *Litomosoides sigmodontis*.

*S. pneumoniae* is surrounded by a capsule composed of complex carbohydrates. This capsule is the primary virulence factor for *S. pneumoniae*, providing a mechanism for the bacteria to prevent destruction by macrophages and polymorphonucleocytes. *S. pneumoniae* also has a cell wall composed of proteins and carbohydrates. The carbohydrate portion of this cell wall has the hapten PC as the major antigenic determinant.

One class of PC conjugates is a hapten PC conjugated to a carrier. A commonly utilized hapten PC, p-diazophenylphosphocholine (DPPC), has been conjugated to protein antigens to produce high affinity phenylphosphocholine-(PPC) specific antibodies; however, unfortunately, these antibodies are not found to be protective against *S. pneumoniae*.

In contrast, conjugates of the phosphocholine ester p-nitrophenyl-6-(O-phosphocholine)hydroxyhexanoate ("EPC") have been shown to elicit a PC-specific antibody response. A method of synthesizing EPC is known as described in Spande, T F, "Synthesis of two novel phosphorylcholine esters for probes in immunogenic studies," *J. Org. Chem.* 45:381-84, 1980. This method, however, is elaborate as it requires many reaction steps to form EPC from the initial reactants 2-bromoethylphosphorodichloridate and tert-butyl 6-hydroxyhexanoate.

Although EPC and a method of synthesizing EPC are known, there is still a need for new methods of synthesizing EPC and derivatives thereof, particularly methods that are more efficient and cost-effective. Additionally, there is a need to develop new phosphocholine conjugates that can effectively prevent microorganism infections, including conjugates of EPC and its derivatives. The present invention is directed to these, as well as other, important needs.

SUMMARY OF THE INVENTION

In one aspect, the present invention is directed to methods, comprising the steps of:

contacting

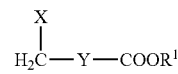

with phosphocholine to form

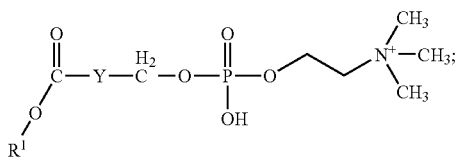

and replacing $R^1$ with

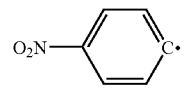

to form

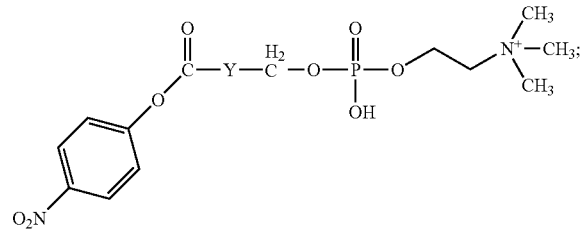

wherein X is bromo, chloro, iodo, tosyl, or mesyl;

$R^1$ is H or alkyl;

Y is —$(CH_2)_n$— optionally substituted at any one or more methylene unit with halo, alkyl, alkenyl, alkynyl, cycloalkyl, alkylcycloalkyl, heterocyclyl, heterocycloalkyl, aryl, aralkyl, aryloxy, heteroaryl, heteroaralkyl, perfluoroalkyl, alkylamido, acyl, acyloxy, alkanesulfonamido, alkoxy, perfluoroalkoxy, alkylamino, carboxamido, carboalkoxy, or carboxyalkyl, or optionally one or more methylene unit is replaced with O, S, or NH, or a combination thereof; and n is an integer from 0 to 20. The replacing step can comprise
reacting

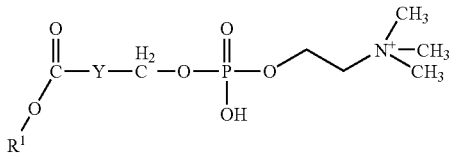

with

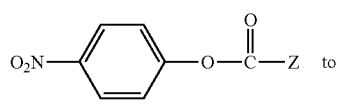

form

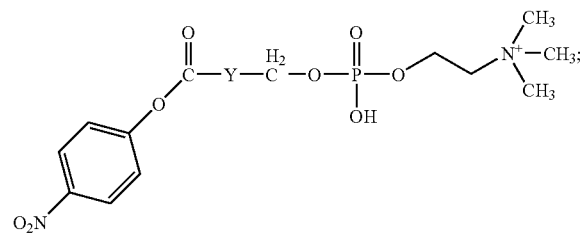

wherein Z is an electron withdrawing group. In some embodiments, the methods produce

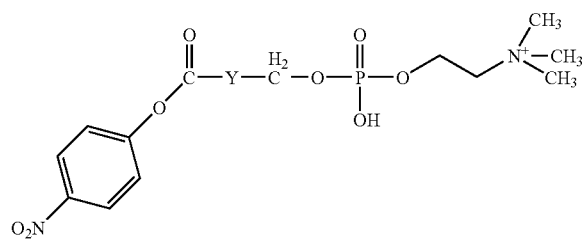

in no more than 2 steps.

In some aspects of the present invention $R^1$ is alkyl and the reacting step comprises deprotecting

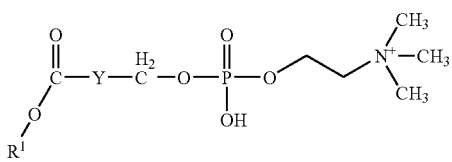

by contacting with a quaternary amine. In some embodiments, the methods produce

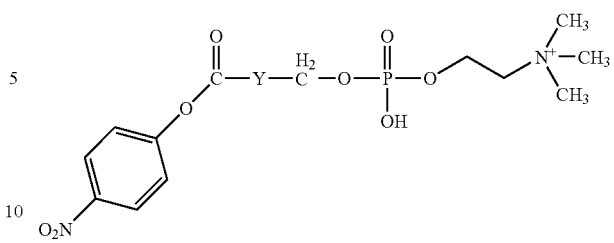

in no more than 3 steps.

In further aspects, the invention provides methods of conjugating the

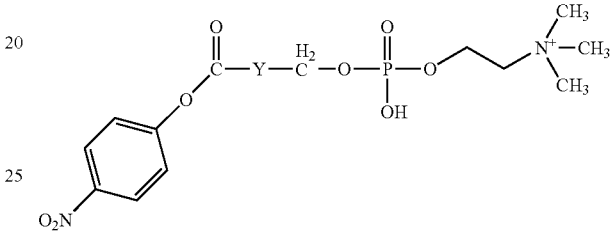

to an immunogenic-carrier having a reactive amino group to form a phosphocholine conjugate.

In still other aspects, the invention provides methods of generating an immune response to PC in a mammal comprising administering a vaccine to a mammal, the vaccine comprising the phosphocholine conjugates formed using the methods of the present invention In still another aspect, the present invention includes the products formed by the methods of the present invention.

The foregoing general description and the following detailed description are exemplary and explanatory only and are not restrictive of the invention, as defined in the appended claims.

DETAILED DESCRIPTION OF ILLUSTRATIVE EMBODIMENTS

As used herein and in the appended claims, the singular forms "a," "an," and "the" include the plural reference unless the context clearly indicates otherwise. Thus, for example, a reference to "a compound" is a reference to one or more compounds and equivalents thereof known to those skilled in the art, and so forth.

The term "alkyl," as used herein, refers to an aliphatic hydrocarbon chain, the hydrocarbon chain can have up to 20 carbon atoms, and preferably 1 to 6 carbon atoms, and more preferably 1 to 4 carbon atoms. The term "alkyl" includes, but is not limited to, straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. In some embodiments, the alkyl group is preferably branched having 3 to 8 carbon atoms. The term "straight chain alkyl" refers to an unbranched alkyl group. The term "lower alkyl" refers to an alkyl group having 1 to 4 carbon atoms.

The term "hapten" as used herein refers to generally small molecules that are not capable of eliciting a strong immune response unless coupled to an immunogenic carrier.

The terms "PC hapten" or "phosphocholine hapten" as used herein refer to a hapten molecule which contains the phosphocholine group.

The terms "PC conjugate" or "phosphocholine conjugate" as used herein refer to a conjugate of a PC hapten with an immunogenic carrier, such as a polypeptide or a protein.

The term "good leaving group" as used herein refers to a group covalently linked to a carbon atom that forms a polarized bond with the carbon atom, thereby resulting in a weak covalent bond. This makes the carbon atom more susceptible to nucleophilic attack. Examples of good leaving group include iodo, chloro, bromo, tosyl and mesyl groups.

The term "electron withdrawing group" as used herein refers to a group covalently linked to a carbon atom that forms a polarized bond, similar to a good leaving group, and can include groups such as nitro, nitrile, carbonyl, and trifluoroacetyl.

The term "immunogenic carrier" as used herein refers to a variety of molecules or substances that allow an immune response to be raised against a hapten molecule when the hapten molecule is attached to the immunogenic carrier. In the case of a PC hapten, when attached to an immunogenic carrier, a PC conjugate is formed. Immunogenic carriers include, for example, soluble proteins, polypeptides and polymer molecules. Proteins such as bovine serum albumen and keyhole limpet hemocyanin (KLH) or synthetic polymers such as polylysine are routinely used. In addition to soluble proteins and polymers, immunogenic carriers also include insoluble substances such as killed microorganisms or fragments thereof. In one example, a phosphocholine hapten may be coupled to the surface of killed *S. pneumoniae* for the purpose of immunizing against infection by this bacterium. The immune response to hapten molecules is described by Berzofsky, J. et al. in Paul, W. E., ed. (1989) *Fundamental Immunology*, Raven Press, New York, pp. 169-208, incorporated herein by reference. Procedures for conjugation of haptens to immunogenic carriers and for immunizations using the hapten:immunogenic carrier conjugates are described in Harlow, E. (1988) *Antibodies: a Laboratory Manual*, Cold Spring Harbor Laboratories, Cold Spring Harbor, N.Y., incorporated herein by reference.

"EPC" is used herein to refer to the phosphocholine ester p-nitrophenyl-6-(O-phosphocholine)hydroxyhexanoate, while "EPC derivatives" is used herein to refer to derivatives of EPC that retain a terminal p-nitrophenyl moiety and a terminal phosphocholine moiety, the two terminals being separated by a spacer —OOC—Y—CH$_2$—, as detailed above. EPC and EPC derivatives can be synthesized by the methods described herein, including reacting an alkanoic acid having a good leaving group substituted on the terminal methylene carbon with a phosphocholine molecule. The good leaving group can be a halogen, tosyl, or mesyl group, but preferably bromine. This reaction forms a phosphocholine alkanoate. The formed phosphocholine alkanoate can be reacted with p-nitrophenyl trifluoroacetate in an esterification process that results in a p-nitrophenyl-O-phosphocholine hydroxyl alkyl ester.

In some embodiments, EPC and EPC derivatives are formed by reacting an alkyl ester derivative of alkanoic acid having a good leaving group substituted on the terminal methylene carbon with a phosphocholine molecule. The formed alkyl phosphocholine alkanoate ester is deprotected by contacting with a quaternary amine, e.g., tetrabutylammonium hydroxide, forming a phosphocholine alkanoate. The formed phosphocholine alkanoate can be reacted with p-nitrophenyl trifluoroacetate in an esterification process that results in a p-nitrophenyl-O-phosphocholine hydroxyl alkyl ester.

In other embodiments of the present invention is directed to methods are provided, comprised of the following steps:

contacting

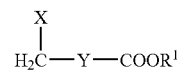

with phosphocholine to form

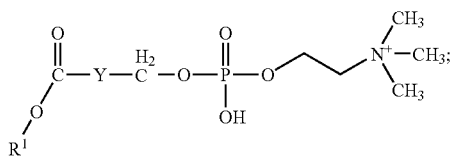

and replacing $R^1$ with

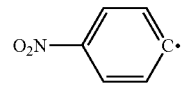

to form

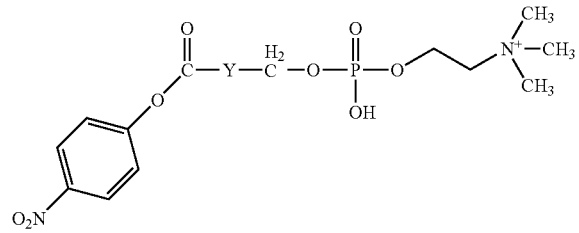

wherein X is bromo, chloro, iodo, tosyl, or mesyl;

$R^1$ is H or alkyl;

Y is —(CH$_2$)$_n$— optionally substituted at any one or more methylene unit with halo, alkyl, alkenyl, alkynyl, cycloalkyl, alkylcycloalkyl, heterocyclyl, heterocycloalkyl, aryl, aralkyl, aryloxy, heteroaryl, heteroaralkyl, perfluoroalkyl, alkylamido, acyl, acyloxy, alkanesulfonamido, alkoxy, perfluoroalkoxy, alkylamino, carboxamido, carboalkoxy, or carboxyalkyl, or optionally one or more methylene unit is replaced with O, S, or NH, or a combination thereof; and n is an integer from 0 to 20. The replacing step can comprise reacting

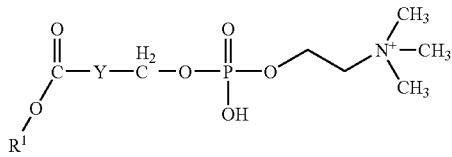

with

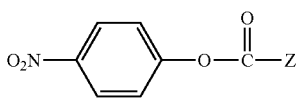

to form

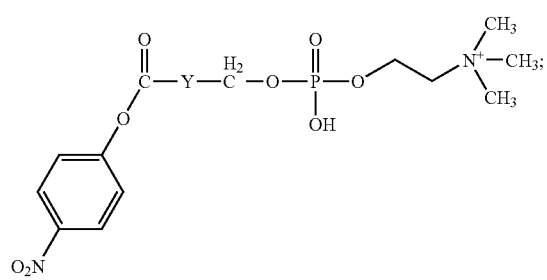

wherein Z is an electron withdrawing group. In some embodiments Z can be trifluoroacetyl. In some embodiments, the methods produce

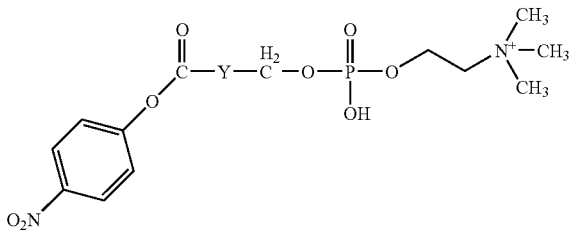

in no more than 2 steps. In some embodiments $R^1$ is H or lower alkyl. In some embodiments Y is —$(CH_2)_n$— and n is an integer from 2-12, and preferably 4. In some embodiments X is bromo. In still other embodiments

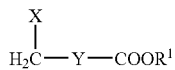

is 6-bromohexanoic acid.

Other embodiments of the present invention, in which $R^1$ is alkyl, the reacting step comprises deprotecting

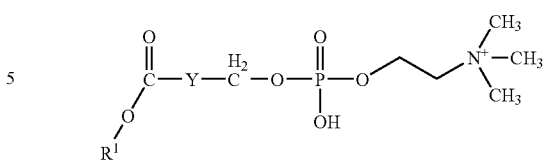

by contacting with a quaternary amine. In a number of embodiments $R^1$ is ethyl. In some embodiments

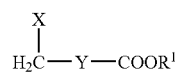

is ethyl-6-bromohexanoate. In some embodiments, the methods produce

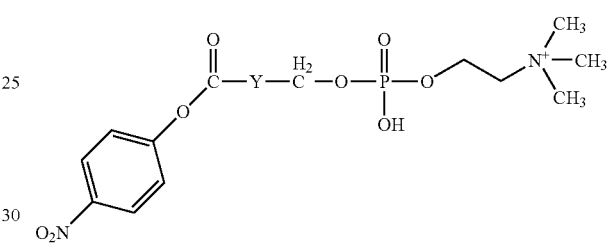

in no more than 3 steps.

In a further aspects, the invention provides conjugating the

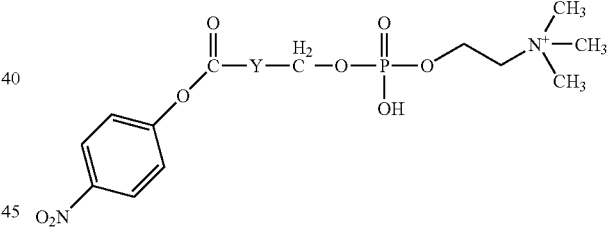

to an immunogenic carrier having a reactive amino group to form a phosphocholine conjugate.

In an alternative method of the present invention, the $R^1$ group can be replaced with a succinimide group. In this method the replacing step comprises reacting according to the following scheme:

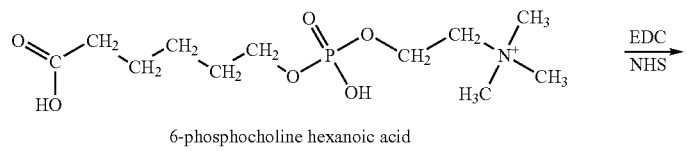

6-phosphocholine hexanoic acid

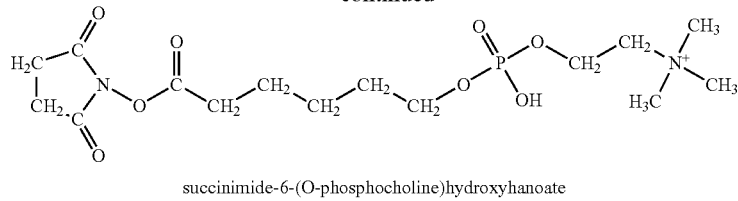

succinimide-6-(O-phosphocholine)hydroxyhanoate

The resulting product, succinimide-6-(O-phosphocholine) hydroxyhexanoate can be conjugated to an immunogenic carrier according to the steps provided in the present invention.

In still other aspects, the invention provides methods of generating an immune response to PC in a mammal comprising administering a vaccine to a mammal, the vaccine comprising the phosphocholine conjugates formed using the methods of the present invention. This generation of PC-specific immune response can aid the host, which can be a mammal, in generating an effective immune response to protect itself from infection by the PC exhibiting microbial pathogen, such as *S. pneumoniae*. In addition to *S. pneumoniae* many other pathogenic microorganisms exhibit PC on their cell surface, which include, for example, *Streptococcus oralis, Streptococcus sanguis, Streptococcus* spp., *Clostridium* spp., *Lactococcus* spp., *Bacillus* spp., *Haemophilus influenzae, Haemophilus aphrophilus, Proteus morganii, Actinomyces naeslundii, Actinobacillus actinomycetemcomitans, Fusobacterium nucleatum, Neisseria meningitidis, Trichinella spiralis, Acanthocheilonema viteae, Leishmania major, Trypanosoma cruzi, Schistosoma mansoni, Diphyllobothrium latum, Toxicara canis* (second stage larvae), *Acanthocheilonema viteae*, and *Litomosoides sigmodontis*. Depending on the particular pathogen of concern, phosphocholine containing conjugates of the present invention can be tailored or fine tuned to elicit a more effective immune response by a host.

In still another aspect, the present invention includes the products formed by the methods of the present invention.

In one embodiment, the EPC compound can be synthesized using the following two step scheme, Scheme 1, below.

Scheme 1, step 1

Formation of 6-(O-phosphocholine)hydroxyhexanoic acid

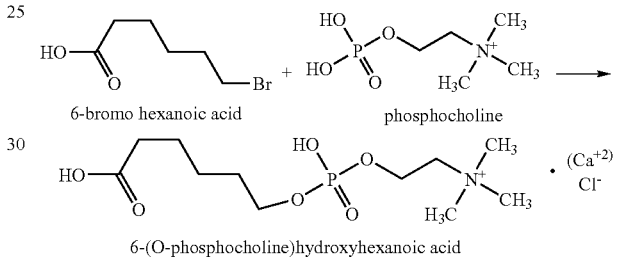

Scheme 1, step 2

Synthesis of 4-nitrophenyl-6-(O-phosphocholine)hydroxyhexanoate

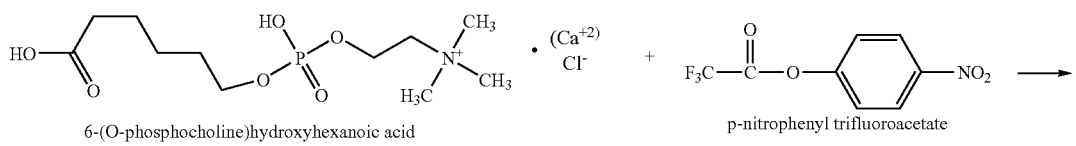

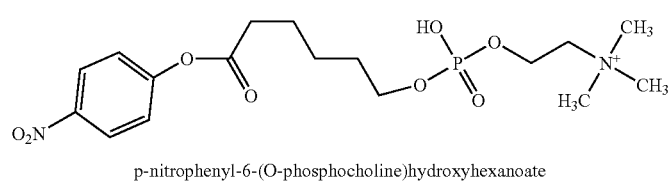

p-nitrophenyl-6-(O-phosphocholine)hydroxyhexanoate

In another embodiment, the EPC compound can be synthesized using the following three step scheme, Scheme 2, below.
Scheme 2, step 1
Formation of ethyl-6-phosphocholinehexanoate
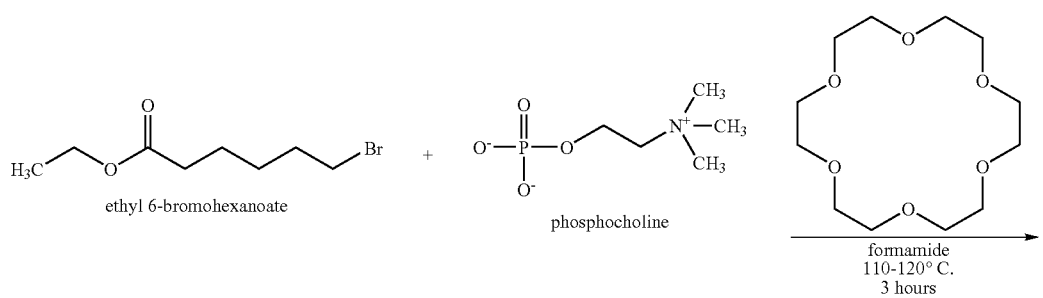
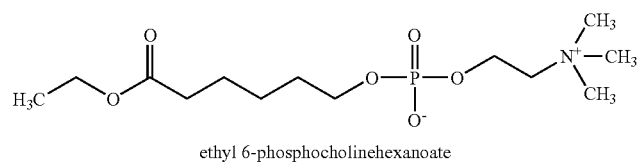
Scheme 2, step 2
Deprotection of ethyl-6-phosphocholinehexanoate
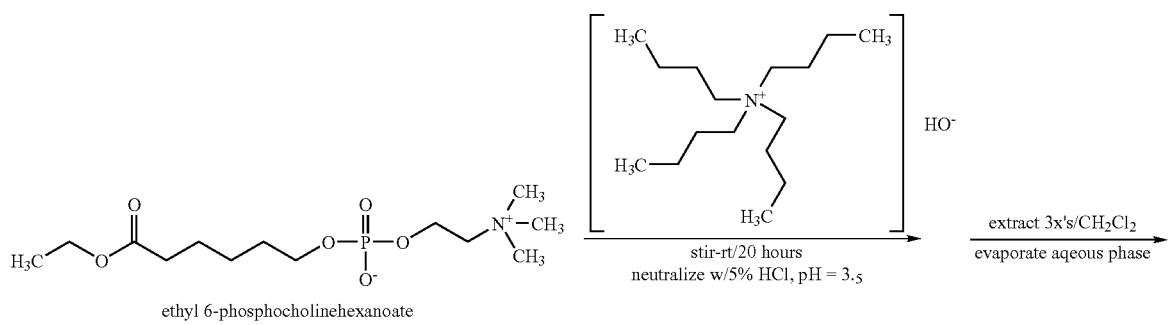
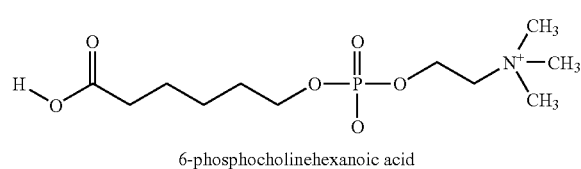

Scheme 2, step 3

Formation of 6-(O-phosphocholine)hydroxyhexanoate

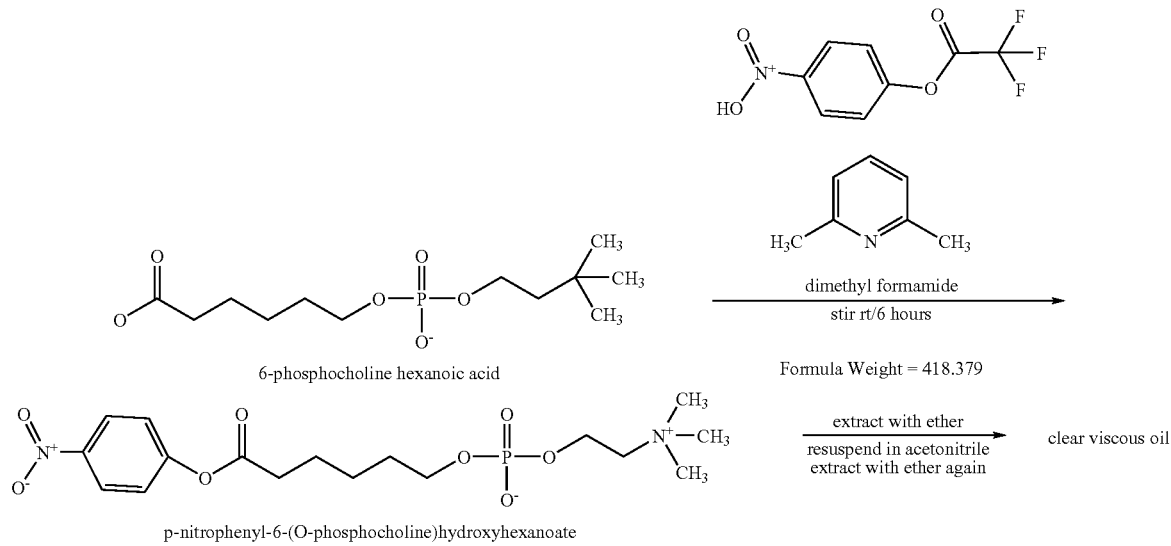

The compounds can be synthesized, for example, by the methods described herein, or variations thereon as appreciated by the skilled artisan. All methods disclosed in association with the present invention are contemplated to be practiced on any scale, including milligram, gram, multigram, kilogram, multikilogram or commercial industrial scale.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed., Wiley & Sons, 1991.

The EPC and EPC derivatives, which are formed from the methods of the present invention, may be conjugated to an immunogenic carrier in order to elicit an immune response in a subject. Preferably, the PC conjugates formed elicit a PC-specific immunogenic response in a subject. The PC conjugates described herein may be used to immunize animals against infection by pathogenic organisms containing PC antigens, such as *S. pneumoniae*, for example.

Conjugates such as EPC-KLH are thought to succeed in inducing a PC-specific response by keeping the PC moiety extended away from the carrier protein by a long straight-chain carbon spacer; whereas in the case of the DPPC antigen, the PC is directly linked to a large immunodominant phenyl ring structure. This dominant phenyl ring causes the response to DPPC-KLH to undergo affinity maturation via the selective amplification of high affinity group II PPC-specific antibodies, which do not use the $V_H1$ gene to encode their H-chains and do not protect vaccinated hosts against *S. pneumoniae*. See Wicker, et al. (1982) *J. Immunol.* 131:2468 and Wicker, et al. (1982) *J. Immunol.* 129:950. In contrast, PC conjugates such as EPC with straight chain linkers are thought to allow for the selection and maturation of presumably low affinity PC-specific (group I) clones that have not been clonally deleted in the xid mice, for example, and have been shown to be protective against *S. pneumoniae* and other pathogens.

Synthesis of PC Conjugates

EPC and EPC derivatives in which the length of the straight chain alkyl group is varied are synthesized by modifications of the synthetic schemes and the detailed methods provided herein. EPC and its derivatives that contain para-nitrophenyl, or other leaving groups known to those of skill in the art, may be conjugated to carriers having amino groups such as proteins, polypeptides, polymers or other immunogenic carriers by a variety of methods. For example, EPC, or EPC derivatives containing 6-para-nitrophenyl, may be conjugated to proteins using the methods described herein, along with other well known methods for conjugating haptens to carrier molecules, such as those described in Harlow, E., *Antibodies; a Laboratory Manual, Cold Spring Harbor Laboratories*, Cold Spring Harbor, N.Y. (1988).

The intermediate 6-(O-phosphocholine)hydroxyhexanoate is formed during the process of synthesizing EPC, according to the methods of the present invention. 6-(O-phosphocholine)hydroxyhexanoate, or derivatives thereof having alkyl groups of varying length, can be used to synthesize a variety of PC analogues that can be conjugated to immunogenic carriers.

Testing of Conjugates

The PC conjugates synthesized as described herein can be tested for their ability to elicit protective antibodies to PC when the conjugates are administered to animals, preferably mammals. A variety of model systems known to those of skill in the art may be used to establish the ability of the conjugates to raise antibodies specific to PC and to provide immunoprotection to the host. These animal model systems generally use three types of experimental protocols to establish immunoprotection: passive transfer of protective antibodies, adoptive transfer of white blood cells, and direct in situ challenge by pathogenic organisms in an appropriately immunized animal.

Animal models for immunocompromised conditions can be used to test the provided PC conjugates, especially considering that there are large patient groups that are immunodeficient in their ability to respond to PC antigens. An example of one type of this animal model is xid mice.

Antisera from animals immunized with the PC conjugates may be tested for their ability to bind *S. pneumoniae* or other microorganisms containing PC in their capsids or cell membranes. Since production of antibodies capable of binding the bacteria is necessary for effective vaccination, the production of antibodies with this capability may be used to test the conjugates for their desirability for use in a vaccine. A variety of bacterial strains may be used, including the WU-2 strain of *S. pneumoniae*.

Pharmaceutical Compositions and Administration of Vaccines

Pharmaceutical compositions of the invention are suitable for use in a variety of drug delivery systems. Pharmaceutically acceptable carriers and formulations for use in the present invention are found in *Remington's Pharmaceutical Sciences*, Mack Publishing Company, Philadelphia, Pa., 17th ed. (1985), which is incorporated herein by reference. For a brief review of methods for drug delivery, see, Langer, *Science* 249:1527-1533 (1990), which is incorporated herein by reference.

The PC conjugates of the present invention can be formed into and used in pharmaceutical vaccine compositions that are useful for administration to mammals, particularly humans. These compositions comprise the PC conjugates and pharmaceutically acceptable carriers. These compositions are suitable for single administrations or a series of administrations. When given as a series, inoculations subsequent to the initial administration are given to boost the immune response and are typically referred to as booster inoculations.

The pharmaceutical compositions of the invention are intended for parenteral, topical, oral, intranasal or local administration. Preferably, the pharmaceutical compositions are administered parenterally, intravenously, subcutaneously, intradermally, intranasally or intramuscularly. Thus, the invention includes compositions for parenteral administration that comprise a solution of the agents described above dissolved or suspended in an acceptable carrier, preferably an aqueous carrier. A variety of pharmaceutically acceptable aqueous carriers may be used, e.g., water, buffered water, 0.4% saline, 0.3% glycine hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable carriers, which are substances that help approximate physiological conditions, such as those that are pH adjusting and buffering agents, tonicity adjusting agents, wetting agents and the like, e.g., sodium acetate, sodium lactate, sodium chloride, potassium chloride, calcium chloride, sorbitan monolaurate, triethanolamine oleate, and the like.

For solid compositions, conventional nontoxic pharmaceutically acceptable carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol administration, the PC conjugates are preferably supplied in finely divided form along with a surfactant and propellant as pharmaceutically acceptable carriers. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides, may be employed. A carrier can also be included, as desired, as with, e.g., lecithin for intranasal delivery.

The PC conjugates of the invention are used prophylactically as vaccines. The vaccines of the invention contain as an active ingredient a PC conjugate. Useful pharmaceutically acceptable carriers are well known in the art, and include, for example, thyroglobulin, albumins such as human serum albumin, tetanus toxoid, polyamino acids such as poly(D-lysine: D-glutamic acid), influenza, hepatitis B virus core protein, hepatitis B virus recombinant vaccine. The vaccines can also contain a physiologically tolerable (acceptable) diluent such as water, phosphate buffered saline, or saline. Furthermore, vaccines typically include an adjuvant, such as incomplete Freund's adjuvant, aluminum phosphate, aluminum hydroxide, or alum are materials well known in the art.

Vaccine compositions containing the PC conjugates of the invention are administered to a patient to elicit a protective immune response against PC hapten and the organisms expressing the PC moiety on their surfaces. A "protective immune response" is one which prevents infection by a bacterium or parasite containing PC in its cell wall. An amount sufficient to accomplish this is defined as an "immunogenically effective dose." Amounts effective for this use will depend on, e.g., the PC conjugate composition, the manner of administration, the weight and general state of health of the patient, and the judgment of the prescribing physician, and the organism against which protection is sought. For example, the vaccines of the present invention may be administered to groups of patients who do not respond well to current polysaccharide based vaccines. Dosages, formulations and administration schedules may vary in these patients compared to normal individuals. In general, dosages range for the initial immunization from about 10 μg to about 1,000 mg of the PC conjugate for a 70 kg patient, followed by boosting dosages of from about 10 μg to about 1,000 mg of the PC conjugate, pursuant to a boosting regimen over weeks to months depending upon the patient's response and condition. The patient's response can be measured, for example, by measuring anti-PC antibodies present in the patients blood at intervals after the initial immunization.

In addition to *S. pneumoniae* many other pathogenic microorganisms exhibit PC on their cell surface, which include, for example, *Streptococcus oralis, Streptococcus sanguis, Streptococcus* spp., *Clostridium* spp., *Lactococcus* spp., *Bacillus* spp., *Haemophilus influenzae, Haemophilus aphrophilus, Proteus morganii, Actinomyces naeslundii, Actinobacillus actinomycetemcomitans, Fusobacterium nucleatum, Neisseria meningitidis, Trichinella spiralis, Acanthocheilonema viteae, Leishmania major, Trypanosoma cruzi, Schistosoma mansoni, Diphyllobothrium latum, Toxicara canis* (second stage larvae), *Acanthocheilonema viteae*, and *Litomosoides sigmodontis*.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods, and examples are illustrative only and not limiting.

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

Step 1: Synthesis of 6-(O-phosphocholine)hydroxyhexanoic acid

A sample of 6-bromohexanoic acid is combined with a catalytic amount of 18-crown-6 in formamide. To this combination, an equal molar amount of phosphorylcholine chloride calcium salt tetrahydrate is added. The resulting mixture is heated to 110-120° C. for about 3 hours. After incubation, the mixture is cooled to room temperature and is applied to a silica gel column (Emerck: 230-400 mesh silica gel; d2.5 cm×L35 cm). The product, 6-(O-phosphocholine)hydroxyhexanoic acid, is eluted from the silica gel column with methanol:water (4:1) solution.

Step 2: Synthesis of p-nitrophenyl-6-(O-phosphocholine)hydroxyhexanoate

A sample of 6-phosphocholinehexanoic acid in dimethylformamide is stirred at room temperature for 5 min. To this mixture, approximately a three fold molar excess of p-nitrophenyl trifluoroacetate is added. While stirring the resulting mixture, approximately a 2 fold molar excess of 2,6-lutidine is added and the mixture is stirred until the 6-phosphocholinehexanoate completely dissolves. The reaction mixture is stirred at room temperature for an additional 6 hours. Afterwards, an aliquot of ethyl ether is added to the reaction mixture to precipitate p-nitrophenyl 6-(O-phosphocholine)hydroxyhexanoate from solution. The supernatant is decanted and the oily product is dissolved in acetonitrile and is precipitated again with ether. After the removal of solvent traces, p-nitrophenyl 6-(O-phosphocholine)hydroxyhexanoate is obtained.

The identity of the final product, p-nitrophenyl 6-(O-phosphocholine) hydroxyhexanoate can be confirmed by mass spectrometry, proton NMR, coupled and decoupled $^{13}C$ NMR and FT-IR.

Example 2

Synthesis of 4-nitrophenyl-6-(O-phosphocholine)hydroxyhexanoate from ethyl 6-bromohexanoate Step 1: Synthesis of ethyl 6-phosphocholinehexanoic acid A sample of 9.1 g (41.2 mmol) of ethyl 6-bromohexanoate was combined with 1.1 g (4.1 mmol) of 18-crown-6 in 40 ml of formamide. To this combination, 9.2 g (41.2 mmol) of phosphorylcholine chloride calcium salt tetrahydrate was added. The resulting mixture was heated to 110-120° C. for about 3 hours. After incubation, the mixture was cooled to room temperature and applied to a silica gel column (Emerck: 230-400 mesh silica gel; d2.5 cm×L35 cm). The product was eluted from the silica gel column with methanol:water (4:1) solution, which yielded 10 grams of ethyl 6-phosphocholinehexanoate with a percentage yield of 74%.

Step 2: Deprotection of ethyl 6-phosphocholinehexanoate to yield 6-phosphocholine hexanoic acid A sample of 2.0 g (6.15 mmol) of ethyl 6-phosphocholinehexnoate was combined with 3.2 g (12.3 mmol) of tetrabutylammonium hydroxide and 8 ml of water. The combination was stirred at room temperature for about 20 hours. After incubation, the pH was adjusted to 3.5 by the addition of 5% aqueous HCl as needed. The mixture was extracted three times with dichloromethane and the aqueous phase was evaporated. The crude product (6-phosphocholinehexanoic acid) was purified by silica gel chromatography, as shown above in Step 1, to yield 0.855 g of purified 6-phosphocholinehexanoic acid at a yield of about 46%. The combined yield of Steps 1 and 2 of the synthesis totaled about 34%.

Step 3: Synthesis of p-nitrophenyl 6-(O-phosphocholine)hydroxyhexanoate

A sample of 505 mg (1.7 mmol) of 6-phosphocholinehexanoic acid in 11 ml of dimethylformamide was stirred at room temperature for 5 min. To this mixture, 1.3 g (5.5 mmol) of p-nitrophenyl trifluoroacetate was added. While stirring the resulting mixture, 0.43 ml (3.7 mmol) of 2,6-lutidine was added and the mixture was stirred until the 6-phosphocholinehexanoate completely dissolved. The reaction mixture was stirred at room temperature for an additional 6 hours. Afterwards, a 150 ml aliquot of ethyl ether was added to the reaction mixture to precipitate p-nitrophenyl 6-(O-phosphocholine)hydroxyhexanoate from solution. The supernatant was decanted and the oily product was dissolved in 5 ml of acetonitrile and precipitated again with ether. After the removal of solvent traces, 571 mg of p-nitrophenyl 6-(O-phosphocholine)hydroxyhexanoate was obtained at a yield of about 80%. The overall synthesis produced a yield of about 27%.

The identity of the final product, p-nitrophenyl 6-(O-phosphocholine) hydroxyhexanoate was confirmed by mass spectrometry, proton NMR, coupled and decoupled $^{13}C$ NMR and FT-IR.

Example 3

Conjugation of PC Haptens

EPC haptens are conjugated to keyhole limpet hemocyanin (KLH) (400,000 used as MW) dissolved in borate buffered saline (BBS), pH 8.5 at 10 mg/ml. EPC is dissolved in dry acetonitrile (100 mg/ml) just prior to addition to the KLH. Hapten and KLH are mixed overnight at 4° C. and then dialyzed to remove unbound hapten and the released p-nitrophenylate. Alternatively, the PC-KLH conjugate can be purified by gel exclusion chromatography on a Sephadex G-25 column. The conjugation efficiency is estimated by determining the phosphate bound to protein according to the method described in Ames, B. N., et al. (1960) *J. Biol. Chem.* 235:769.

Example 4

Eliciting Immune Response to PC in a Mammal

Mice for purposes of determining an immune response to the PC conjugates formed by the methods described herein can be obtained from a number of sources, including CBA/N, (CBA/n X DBA/2)F1, and BALB/c mice from the Small Animal Facility, NIH, Bethesda, Md.; breeding pairs of the consomic xid C.CBA/N mice from Dr. Carl Hansen, Division of Veterinary Medicine, NIH, Bethesda, Md.

In general, mice are immunized i.p. with 200 μg of the synthesized EPC conjugates (or EPC derivative conjugates) prepared as described above in Example 3. The immunized mice can then be bled on day 7 for primary response serum and then can be boosted with another 200 μg of antigen in IFA on day 14, which can be followed by bleeding on day 21 to obtain 2° response serum. Phenotypically normal CDF1 female and immune defective CDF1 male xid mice can be immunized and boosted according to the above schedule, and their serum can be analyzed at 7 days after the secondary immunization. The PC response can be determined according to the materials and methods shown in U.S. Pat. No. 5,455,032, which is hereby incorporated by reference in its entirety.

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method, comprising the steps of:

contacting

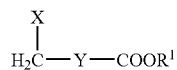

with a calcium salt of phosphocholine to form

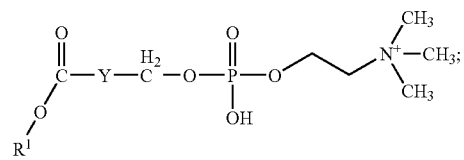

and reacting said

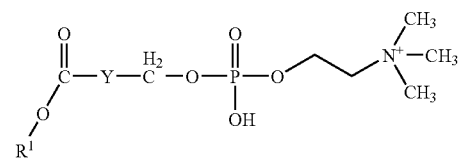

with

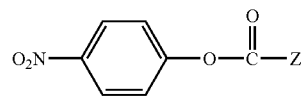

to form

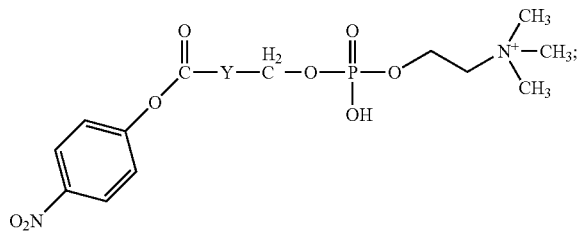

wherein

X is bromo, chloro, iodo, tosyl, or mesyl;

$R^1$ is H or alkyl;

Y is —$(CH_2)_n$— optionally substituted at any one or more methylene unit with halo, alkyl, alkenyl, alkynyl, cycloalkyl, alkylcycloalkyl, heterocyclyl, heterocycloalkyl, aryl, aralkyl, aryloxy, heteroaryl, heteroaralkyl, perfluoroalkyl, alkylamido, acyl, acyloxy, alkanesulfonamido, alkoxy, perfluoroalkoxy, alkylamino, carboxamido, carboalkoxy, or carboxyalkyl, or optionally one or more methylene unit is replaced with O, S, or NH, or a combination thereof;

n is an integer from 0 to 20; and

Z is an electron withdrawing group.

2. The method of claim 1, wherein X is bromo.

3. The method of claim 1, wherein $R^1$ is H.

4. The method of claim 1, wherein Y is —$(CH_2)_n$— and n is an integer from 2-12.

5. The method of claim 1, wherein Y is —$(CH_2)_n$— and n is 4.

6. The method of claim 1, wherein X is bromo, $R^1$ is H, Y is —$(CH_2)_n$— and n is 4.

7. The method of claim 1, wherein

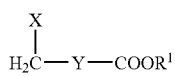

is 6-bromohexanoic acid.

8. The method of claim 1, wherein Z is trifluoroacetyl.

9. The method according to claim 1, further comprising the step of:

conjugating

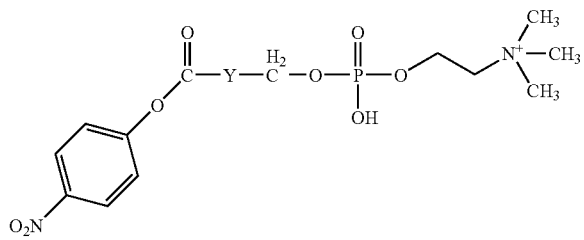

the to an immunogenic carrier having a reactive amino group to form a phosphocholine conjugate.

10. The method of claim 1, wherein $R^1$ is alkyl and the reacting step further comprises deprotecting

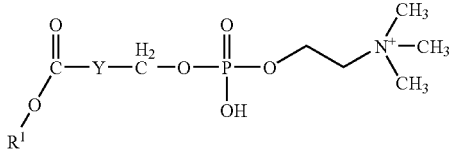

by contacting with a quaternary amine.

11. The method of claim 10, wherein X is bromo.

12. The method of claim 10, wherein $R^1$ is ethyl.

13. The method of claim 10, wherein Y is —$(CH_2)_n$— and n is an integer from 2-12.

14. The method of claim 10, wherein Y is —$(CH_2)_n$— and n is 4.

15. The method of claim 10, wherein Z is trifluoroacetyl.

16. The method of claim 10, wherein X is bromo, $R^1$ is ethyl, Y is —$(CH_2)_n$—, Z is trifluoroacetyl and n is 4.

17. The method of claim 10, wherein

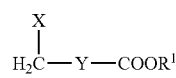

is ethyl-6-bromohexanoate.

18. The method of claim 10, wherein the quaternary amine is tetrabutylammonium hydroxide.

19. The method according to claim 10, further comprising the step of:

conjugating the

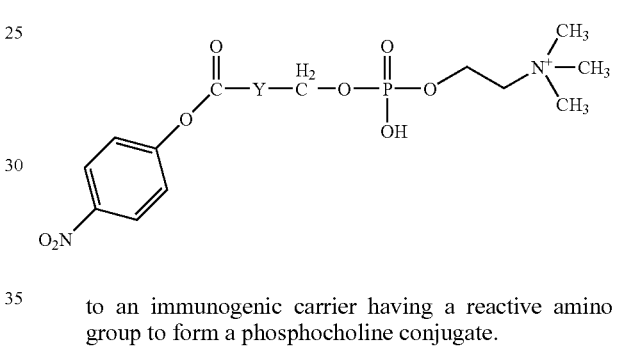

to an immunogenic carrier having a reactive amino group to form a phosphocholine conjugate.

\* \* \* \* \*